United States Patent [19]

Bustos et al.

[11] Patent Number: 5,691,143
[45] Date of Patent: Nov. 25, 1997

[54] AMPLIFICATION AND DETECTION OF THE ALPHA ANTIGEN GENE OF MYCOBACTERIUM AVIUM COMPLEX SPECIES

[75] Inventors: Silvia A. Bustos, Catonsville; Christine A. Rostkowski; Keith C. Williams, both of Baltimore; Leslie A. Stringfellow, Mt. Airy, all of Md.

[73] Assignee: Becton, Dickinson and Company, Franklin Lakes, N.J.

[21] Appl. No.: 616,398

[22] Filed: Mar. 15, 1996

[51] Int. Cl.⁶ .................... C07H 21/04; C12Q 1/68; C12P 19/34
[52] U.S. Cl. .................... 435/6; 435/91.2; 536/24.3; 536/24.32; 536/24.33
[58] Field of Search .................... 435/6, 91.2; 536/24.3, 536/24.32, 24.33

[56] References Cited

U.S. PATENT DOCUMENTS 5,422,252  6/1995  Walker et al. .................... 435/91.2
5,470,723  11/1995 Walker et al. .................... 435/91.2

OTHER PUBLICATIONS

Takano et al., Scand. J. Immunol. 40, 165–170 (1994).
Kitaura et al., Biochem. Biophys. Res. Comm. 196(3), 1466–1473 (1993).
De Wit et al., DNA Seq. 4(4), 267–270 (1994) (Abstract only).
C. Abou-Zeid, et al. "Characterization of Fibronectin-Binding Antigens Released by Mycobacterium tuberculosis and Mycobacterium bovis BCG" *Inf. Imm.* 56:3046–3051 (1988).

P. Andersen, et al. "Proteins Released from Mycobacterium tuberculosis during Growth" *Inf. Imm.* 59:1905–1910 (1991).

N. Ohara, et al. "Cloning and Sequencing of the gene for α Antigen from Mycobacterium avium and Mapping of B–Cell Epitopes" *Inf. Imm.* 61:1173–1179 (1993).

L. Lima, et al. "Nucleotide sequence of the gene coding for the 85–B antigen of Mycobacterium leprae" *Nucl. Acids Res.* 19:5789 (1991).

K. Matsuo, et al. "Cloning and Expression of the Gene for the Cross-Reactive α Antigen of Mycobacterium kansasii" *Inf. Imm.* 58:550–556 (1990).

K. Matsuo, et al. "Cloning and Expression of the Mycobacterium bovis BCG Gene for Extracellular α Antigen" *J. Bacteriol.* 170:3847–3854 (1988).

H. G. Wiker, et al. "Evidence for Three Separate Genes Encoding the Peroteins of the Mycobacterial Antigen 85 Complex" *Inf. Imm.* 58:272–274 (1990).

H. Saito, et al. "Identification of Various Serovar Strains of Mycobacterium avium Complex by Using DNA Probes Specific for Mycobacterium avium and Mycobacterium intracellulare" *J. Clin. Microbiol.* 28:1694–1697 (1990).

*Primary Examiner*—Kenneth R. Horlick

[57] ABSTRACT

Oligonucleotide primers derived from the BCG-85B gene of mycobacteria and methods for complex-specific amplification of a fragment of the BCG-85B gene in species of the *Mycobacterium avium* Complex (MAC) are provided. Also disclosed are an oligonucleotide detector probe useful for detecting the amplification products of the BCG-85B gene in MAC species and adaptation of the primers for multiplex amplification reactions.

25 Claims, No Drawings

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

TTGAATAGTT TCTTACAAGT TGACGATCCT CGGCGAT 37

( 2 ) INFORMATION FOR SEQ ID NO:2:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

TTGAATAGTT TCTTACAAGT TGACAGAGCG ATCCGGC 37

( 2 ) INFORMATION FOR SEQ ID NO:3:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

ACCGCATCGA ATGCATGTCT CGGGGATCCT CGGCGAT 37

( 2 ) INFORMATION FOR SEQ ID NO:4:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

ACCGCATCGA ATGCATGTCT CGGGGGATCC TCGGCGAT 38

( 2 ) INFORMATION FOR SEQ ID NO:5:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

ACCGCATCGA ATGCATGTCT CGGGCGGATC CTCGGCGAT 39

( 2 ) INFORMATION FOR SEQ ID NO:6:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

ACCGCATCGA ATGCATGTCT CGGGCCGGAT CCTCGGCGAT 40

( 2 ) INFORMATION FOR SEQ ID NO:7:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CGATTCCGCT CCAGACTTCT CGGGAGAGCG ATCCGGC 37

( 2 ) INFORMATION FOR SEQ ID NO:8:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CGATTCCGCT CCAGACTTCT CGGGGAGAGC GATCCGGC 38

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CGATTCCGCT CCAGACTTCT CGGGCGAGAG CGATCCGGC 39

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CGATTCCGCT CCAGACTTCT CGGGCCGAGA GCGATCCGGC 40

( 2 ) INFORMATION FOR SEQ ID NO:11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CAACGCCGCA GTC 13

( 2 ) INFORMATION FOR SEQ ID NO:12:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GACGGGTCGA GCA                                                                                          13

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GATCCTGGCC GTCAA                                                                                        15

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

TCCTGACCAG CGAGCTG                                                                                      17

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CCGGCGTCAC CCATCGCC                                                                                     18

( 2 ) INFORMATION FOR SEQ ID NO:16:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

ACCGCATCGA ATGCATGTCT CGGGTGTACT GAGATCCCCT                                                             40

( 2 ) INFORMATION FOR SEQ ID NO:17:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GAGAGCGATC CGGCAAGGCG TACTCGACC                                                                         29

( 2 ) INFORMATION FOR SEQ ID NO:18:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (xi) SEQUENCE DESCRIPTION: SEQ ID NO:18:

GTACTGAGAT CCCCTGGATC CTCGGCGAT  29

AMPLIFICATION AND DETECTION OF THE ALPHA ANTIGEN GENE OF MYCOBACTERIUM AVIUM COMPLEX SPECIES

FIELD OF THE INVENTION

The present invention relates to amplification and detection of target nucleic acidsequences. In particular, the invention relates to amplification and detection of target nucleic acid sequences in mycobacteria.

Background of the Invention

The mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis* and *M. tuberculosis*. Certain of these organisms are the causative agents of disease. For the first time since 1953, cases of mycobacterial infections are increasing in the United States. Although tuberculosis is of particular concern, other mycobacterial infections are also increasing as a result of an increase in the number of immune compromised patients. Many of these new cases are related to the AIDS epidemic, which provides an immune compromised population which is particularly susceptible to infection by mycobacteria. *Mycobacterium avium, Mycobacterium kansasii* and other non-tuberculosis mycobacteria are found as opportunistic pathogens in HIV infected and other immune compromised patients.

*M. avium* and *M. intracellulare* are members of the *Mycobacterium avium* complex (MAC). *M. paratuberculosis* is a subspecies of *M. avium* and is also generally included in the MAC. These species have become important in recent years because of the high prevalence of disseminated MAC infection in AIDS patients. Disseminated MAC infections have been cited as the cause of most of the systemic bacterial infections in patients with HIV, and it has been suggested that most AIDS patients will develop such infections if they survive long enough to become severely immunocompromised. The *Mycobacterium avium* complex is comprised of 28 serovars which are distinguishable on the basis of their biochemical and seroagglutination characteristics (see review by Inderlied, et al. 1993. *Clin. Microbial. Rev.* 6, 266–310). Depending on the method of classification, 10–12 of the 28 serovars are classified as belonging to the species *Mycobacterium avium*, and 10–12 belong to the species *Mycobacterium intracellulare*. Six of the MAC serovars were not definitively classified. MAC infections currently account for approximately 50% of the pathogenic isolates identified by mycobacteriology labs and are most common among AIDS and other immunocompromised patients. Early diagnosis and treatment of MAC infections can improve and prolong the lives of infected individuals.

The diagnosis of mycobacterial infections has traditionally been dependent on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one or two weeks. However, there is still a need to reduce the time required for diagnosing mycobacterial infections to less than a week, preferably to one day or less. Nucleic acid amplification is a powerful technology which allows rapid detection of specific target sequences. It is therefore a promising technology for rapid detection and identification of mycobacteria. Examples of nucleic acid amplification technologies known in the art are Polymerase Chain Reaction (PCR: U.S. Pat. Nos. 4,683,195; 4,683,202; 4,800,159; 4,965,188), Strand Displacement Amplification (SDA) (G. Walker, et at. 1992. *Proc. Nat. Acad Sci. USA* 89, 392–396; G. Walker, et al. 1992. *Nucl. Acids Res.* 20, 1691–1696; U.S. Pat. No. 5,270,184; U.S. Pat. No. 5,455,166; published European Patent Application No. 0 684 315), nucleic acid sequence based amplification (NASBA: U.S. Pat. No. 5,130,238 to Cangene), transcription based amplification (D. Kwoh, et at. 1989. *Proc. Nat. Acad. Sci. USA* 86, 1173–1177), self-sustained sequence replication (3SR: J. Guatelli, et al. 1990. *Proc. Nat. Acad Sci. USA* 87, 1874–1878) and the Qβ replicase system (P. Lizardi, et at. 1988. *BioTechnology* 6, 1197–1202).

Isothermal amplification methods such as SDA and 3 SR have particular advantages in diagnostics, as they do not require the high/low temperature cycling characteristic of methods such as the PCR. They are therefore simpler protocols and require less specialized equipment to perform. However, isothermal amplification methods such as SDA generally are not capable of amplifying targets as large as those amplifiable by PCR. Small target sequences severely restrict the ability to design primers and probes with the desired specificity for detection of a given target because the proximity of appropriate amplification primer binding sites becomes a factor and there is less sequence available in the amplification product for assay probe design.

Initially, SDA was developed for use at temperatures between about 35° C. and 45° C. ("conventional SDA"). Recently, it has been adapted to higher temperatures using thermophilic polymerases and restriction endonucleases ("thermophilic SDA" or "tSDA") as described in published European Patent Application No. 0 684 315. The tSDA system provides the advantages of increased speed and specificity as compared to conventional SDA. While the target binding sequences of amplification primers designed for use in conventional SDA generally will function in tSDA, they are usually shorter and amplification efficiency may therefore be reduced at the higher temperatures of tSDA. Also, as is the case for primer design in conventional SDA, apparently minor modifications in the target binding sequence of primers for tSDA (such as lengthening it) often have unpredictable effects on amplification efficiency. In contrast, primers comprising the target binding sequences of primers designed for tSDA usually function efficiently when adapted to amplification primers for conventional SDA or other amplification reactions.

The BCG 85 complex of mycobacteria consists of three antigens (A, B and C) and is produced in large quantities in the first stages of mycobacterial growth. These proteins are believed to play an important role in immunopathology, as they induce gamma interferon synthesis, bind to fibronectin and stimulate cellular and humoral immunity. BCG 85-B corresponds to the alpha antigen. The gene encoding BCG 85-B was originally cloned from *M. bovis* (K. Matsuo, et at. 1988. *J. Bacteriol.* 170:3847–3854) and *M. kansasii* (K. Matsuo, et al. 1990. *Infect. Immun.* 58:550–556). A similar gene was subsequently identified in *M. leprae* (L. Lima, et al. 1991. *Nucl. Acids Res.* 19:5789) and was recently reported in *M. avium* (N. Ohara, et al. 1993. *Infect. Immun.* 61:1173–1179). Two *M. avium*-specific epitopes have been identified in the *M. avium* alpha antigen protein by constructing a series of protein deletions. These *M. avium*- specific epitopes were mapped at Gly-169 to Gln-319 and Leu-318 to Gly-330 in the amino acid sequence.

Certain terms used herein are defined as follows:

An amplification primer is a primer for amplification of a target sequence by extension of the primer after hybridization to the target sequence. The 3' end of an SDA amplification primer (the target binding sequence) hybridizes at the 3' end of the target sequence. The target binding sequence confers target specificity on the amplification pier. The SDA amplification primer further comprises a recognition site for a restriction endonuclease near its 5' end. The recognition site is for a restriction endonuclease which will nick one strand of a DNA duplex when the recognition site is hemimodified, as described by G. Walker, et al. (1992. PNAS, supra). The SDA amplification primer may also be referred to as the "S" primer (e.g., $S_1$ and $S_2$ when a pair of amplification primers is used for amplification of a double stranded sequence). As the target binding sequence is the portion of a primer which determines its target-specificity, for amplification methods which do not require specialized sequences at the ends of the target, the amplification primer generally consists essentially of only the target binding sequence. For example, amplification of a target sequence according to the invention using the PCR will employ amplification primers consisting of the target binding sequences of the amplification primers in Table 1. For amplification methods which require specialized sequences other than a restriction endonuclease recognition site appended to the target (e.g., an RNA polymerase promoter for 3SR, NASBA or transcription based amplification), the required specialized sequence may be linked to the target binding sequence shown in Table 1 using routine methods such as chemical synthesis for preparation of the oligonucleotides.

A bumper primer or external primer is a primer used to generate targets which can be amplified by SDA. The bumper primer anneals to a target sequence upstream of the amplification primer such that extension of the bumper primer displaces the downstream amplification primer and its extension product. Bumper primers may also be referred to as "B" primers (e.g., $B_1$ and $B_2$ when a pair of bumper primers is used to displace the extension products of a pair of amplification primers). Extension of bumper primers is one method for displacing the extension products of amplification palmers, but heating is also suitable in certain amplification reactions.

The terms target or target sequence refer to nucleic acid sequences to be amplified. These include the original nucleic acid sequence to be amplified, the complementary second strand of the original nucleic acid sequence to be amplified, and either strand of a copy of the original sequence which is produced by the amplification reaction. These copies also serve as amplifiable target sequences by virtue of the fact that they comprise copies of the original target sequences to which the amplification primers hybridize.

Copies of the target sequence which are generated during the amplification reaction are referred to as amplification products, amplimers or amplicons.

The term extension product refers to the single-stranded copy of a target sequence produced by hybridization of an amplification primer and extension of the amplification primer by polymerase using the target sequence as a template.

The term assay probe refers to any of the oligonucleotides used in the detection or identification portion of an assay. In the present invention, the assay probes are probes used for complex-, group- or species-specific detection or identification of mycobacteria. Detector probes and capture probes are examples of assay probes.

The assay region or assay region sequence is the portion of a target sequence, or other nucleic acid, to which an assay probe hybridizes.

The term species-specific refers to detection or amplification in a species of organism without substantial detection or amplification in other species of the same genus or species of a different genus. Genus-specific refers to detection or amplification in the majority of the species of a genus, without substantial detection or amplification in the species of a different genus. Group- or complex-specific refers to detection or amplification in a majority of related species in a selected group (e.g., MAC) without substantial detection or amplification in other species of the same genus or species of a different genus.

SUMMARY OF THE INVENTION

The present invention provides oligonucleotide primers which may be used for complex-specific amplification of a target sequence found in all 28 serovars comprising the MAC. The target sequence is a 63 nucleotide segment (nucleotides 506–568) of the BCG 85-B gene which encodes a portion of the alpha antigen of mycobacteria. Thus, a single pair of amplification primers amplifies a target sequence from the BCG 85-B gene of both M. avium and M. intracellulare. Also provided is a detector probe which hybridizes to the assay region of both M. avium and M. intracellulare. Because of sequence variations between these two species, species-specific assay probes may also be designed. The inventive primers also allow amplification and detection of the BCG 85-B target sequence in *M. paratuberculosis*, a subspecies of *M. avium* associated with Crohn's disease in humans and Johne's disease in livestock.

DETAILED DESCRIPTION OF THE INVENTION

Amplification primers and assay probes which allow complex-specific amplification and detection of a target fragment of the BCG 85-B gene of MAC species are provided. The present invention also provides oligonucleotide probes and primers which are particularly useful for amplification of MAC-specific targets in the BCG 85-B gene by Strand Displacement Amplification (SDA). Amplification of the target may be detected as an indication of the presence of a MAC target or identification of the particular MAC species from which the target derived. It has been discovered that the primers of the invention efficiently amplify both *M. avium* and *M. intracellulare* targets in spite of nucleotide sequence differences between these species in the targets at the site of amplification primer hybridization, allowing detection of as few as 10–100 initial copies of the target for either *M. avium* or *M. intracellulare* in SDA. The amplified target sequences may be detected by hybridization to the assay probes of the invention.

Initially, to obtain comparative sequence information, the BCG 85-B genes of mycobacteria other than *M. avium* were amplified by PCR using SEQ ID NO:14 and SEQ ID NO:15 of Table 1 as amplification primers. The amplified region of the gene was between nucleotides 418 and 635 of the *M. avium* sequence. The amplification products were then sequenced and the sequences thus obtained were aligned for primer design. Examples of primers developed for use with SDA are shown in Table 1. Also shown is a probe for detection of the MAC targets. The exemplary restriction endonuclease recognition sites in the amplification primers (HincII for conventional SDA and BsoBI for tSDA) are bolded and the target binding sequences which coffer target specificity (i.e., complex-specificity) are italicized. The BCG 85-B gene sequences to which the upstream amplification primers (SEQ ID NO:1 and SEQ. ID NO:3–6) hybridize in *M. avium* is a perfect Watson-Crick complement. with strain ATCC 15769 but exhibits a single nucleotide mismatch with *M. intracellulare* ATCC 13950 at the 5' end. The primer sequences show several nucleotide mismatches with the sequences of other mycobacteria.

fied. Thus, the terminal sequences of the modified targets in both *M. avium* and *M. intracellulare* become identical, but the assay regions between the sequences which bind the amplification primers will remain unchanged, allowing the amplification products of *M. avium* and *M. intracellulare* to be distinguished. Applicants hypothesize that this unique feature of nucleic acid amplification allows the amplification reaction to overcome the detrimental effects of primer/target mismatches as long as there is sufficient hybridization of the mismatched primer to the target to generate a modified target suitable for amplification. This may account for the high

TABLE 1

| Amplification Primers | | |
|---|---|---|
| 85B-S1 | 5'TTGAATAGTTTCTTACAAGTTGACGATCCTCGGCGAT3' (SEQ ID NO: 1) | |
| 85B-S20 | 5'TTGAATAGTTTCTTACAAGTTGACAGAGCGATCCGGC3' (SEQ ID NO: 2) | |
| 85B-ST1 | 5'ACCGCATCGAATGCATGTCTCGGGGATCCTCGGCGAT3' (SEQ ID NO: 3) | |
| 85B-ST1.1 | 5'ACCGCATCGAATGCATGTCTCGGGGGATCCTCGGCGAT3' (SEQ ID NO: 4) | |
| 85B-ST1.2 | 5'ACCGCATCGAATGCATGTCTCGGGCGGATCCTCGGCGAT3' (SEQ ID NO: 5) | |
| 85B-ST1.3 | 5'ACCGCATCGAATGCATGTCTCGGGCCGGATCCTCGGCGA3' (SEQ ID NO: 6) | |
| 85B-ST2 | 5'CGATTCCGCTCCAGACTTCTCGGGAGAGCGATCCGGC3' (SEQ ID NO: 7) | |
| 85B-ST2.1 | 5'CGATTCCGCTCCAGACTTCTCGGGGAGAGCGATCCGGC3' (SEQ ID NO: 8) | |
| 85B-ST2.2 | 5'CGATTCCGCTCCAGACTTCTCGGGCGAGAGCGATCCGGC3' (SEQ ID NO: 9) | |
| 85B-ST2.3 | 5'CGATTCCGCTCCAGACTTCTCGGGCCGAGAGCGATCCGGC3' (SEQ ID NO: 10) | |
| Bumper Primers | | |
| 85B-B1.2 | 5'CAACGCCGCAGTC3' | (SEQ ID NO: 11) |
| 85B-B2 | 5'GACGGGTCGAGCA3' | (SEQ ID NO: 12) |
| Detector Probe | | |
| 85B-D1 | 5'GATCCTGGCCGTCAA3' | (SEQ ID NO: 13) |
| PCR Primers | | |
| 85b-7 | 5'TCCTGACCAGCGAGCTG3' | (SEQ ID NO: 14) |
| 85b-8 | 5'CCGGCGTCACCCATCGCC3' | (SEQ ID NO: 15) |

SEQ ID NO:1 and SEQ ID NO:2 are useful in conventional SDA reactions for complex-specific amplification of the target. The amplification primers for tSDA were tested in pairwise combinations (SEQ ID NOs:3–6 with SEQ ID NOs:7–10) to confirm amplification. of MAC targets. All primer pairs tested amplified the target to detectable levels, and were then screened for assay sensitivity. SEQ ID NO:1 and SEQ ID NO:2 exhibited the highest amplification efficiency in conventional SDA, whereas SEQ ID NO:4 and SEQ ID NO:8 exhibited the highest amplification efficiency in tSDA. The sensitivity of detection of the BCG 85-B targets in both *M. avium* and *M. intracellulare* using the SEQ ID NO:4 SEQ ID NO:8 amplification primer pair was estimated to be between 10 and 100 initial genomes. The presence of nucleotide mismatches would be expected to destabilize the primer-target complex as compared to a perfectly complementary complex, but amplification efficiency did not appear to be significantly reduced. Initial hybridization of amplification primers to a target sequence in an amplification reaction and extension of the amplification primers produces copies of the desired target sequence flanked by perfectly complementary sequences contributed by the amplification primers. Mismatches are therefore corrected and these terminally-modified targets are ampliefficiency of amplification observed in this system in spite of the mismatch. Further routine optimization of the amplification and detection reaction conditions would be expected to even further increase assay sensitivity.

The amplification primers of the invention are also useful in other nucleic acid amplification protocols such as the PCR, conventional SDA, 3SR, NASBA and TAS. Specifically, any amplification protocol which utilizes specific hybridization of primers to the target sequence, extension of the primers using the target sequence as a template and separation or displacement of the extension products from the target sequence may employ the amplification primers of the invention. For amplification methods which do not require specialized, non-target binding sequences (e.g., PCR), the amplification primers may consist only of the target binding sequences of the amplification primers listed in Table 1. The primer sequences illustrated in Table 1 comprise a specialized, non-target binding sequence (the restriction endonuclease recognition site) which is required for SDA and is appended to the target in the target generation reaction which precedes amplification by SDA. Amplification methods which require other specialized, non-target binding sequences linked to the target (e.g., the RNA polymerase promoter required by 3SR, NASBA and TAS) may employ amplification primers comprising the target binding sequences disclosed herein appended to the sequence required by the selected amplification method. Similarly, a different restriction endonuclease recognition site appropriate for conventional SDA or tSDA may be substituted for the exemplified restriction endonuclease recognition site. These adaptations of the target binding sequences of the invention require only conventional methods for preparation of oligonucleotides of defined sequence (e.g., chemical synthesis) and knowledge readily available to one skilled in the art relating to the structural requirements for the primers of the selected amplification reaction. The target binding sequences of the invention may therefore be readily adapted to MAC-specific target amplification and detection in a variety of amplification reactions using only routine methods for production, screening and optimization.

The primers of the invention are also useful in amplification reactions in which multiple, different targets are simultaneously amplified (multiplex amplification or multiplexing). For example, multiplex amplification using SDA is described in U.S. Pat. No. 5,470,723 and U.S. Pat. No. 5,422,252, the disclosures of which are hereby incorporated by reference. As disclosed therein, using adapter primers a terminal sequence of the BCG 85-B target may be appended to one end of a second target, and a terminal sequence of the second target may be appended to one end of the BCG 85-B target. For example, to produce an adapter primer the 5' end of the target binding sequence of a BCG 85-B amplification primer disclosed herein may be linked to an adapter sequence which is substantially identical to the target binding sequence of an amplification primer for the second target. For the second target, the adapter primer comprises a 3' target binding sequence which hybridizes to the second target and a 5' sequence which is substantially identical to the target binding sequence of an amplification primer for BCG 85-B. After appending a terminal segment of each target to one end of the other, they may be simultaneously amplified using a single pair of amplification primers comprised of the BCG 85-B amplification primer and the amplification primer for the second target. For example, the primers of the invention may be used with IS6110 amplification primers and appropriate adapter primers to simultaneously amplify species-specific (*M. tuberculosis*) and complex-specific (MAC) targets with identification of the group or species in the detection portion of the assay. Alternatively, the primers of the invention may be used with 16S primers and appropriate adapter primers to simultaneously amplify Mycobacterium genus-specific and MAC complex-specific targets, with group-specific identification of MAC or genus-specific identification of mycobacteria in the detection portion of the assay.

The structure and function of the primers used in adapter-mediated multiplexing are described in U.S. Pat. No. 5,470,723 and U.S. Pat. No. 5,422,252. Using these teachings, the target binding sequences of the BCG 85-B amplification primers of the invention may be appended to adapter sequences using routine methods for primer construction and used for multiplex amplification of the BCG 85-B target and any selected second target. For example, the primers of the invention and the primers disclosed in the above patents may be adapted for tSDA multiplex amplification of MAC-specific targets (BCG 85-B) and *M. tuberculosis* (M.tb) species-specific targets (IS6110), for example using the multiplex palmer set shown in Table 2. Target binding sequences are italicized, restriction endonuclease recognition silos are bolded and adapter sequences are underlined:

TABLE 2

| |
|---|
| M.tb Amplification Primer |
| ACCGCATCGAATGCATGTCTCGGGTGTACTGAGATCCCCT (SEQ ID NO: 16) |
| M.tb Adapter Primer |
| GAGAGCGATCCGGCAAGGCGTACTCGACC (SEQ ID NO: 17) |
| MAC Amplification Primer |
| 5'CGATTCCGCTCCAGACTTCTCGGGGAGAGCGATCCGGC3' (SEQ ID NO: 8) |
| MAC Adapter Primer |
| GTACTGAGATCCCCTGGATCCTCGGCGAT (SEQ ID NO: 18) |

The MAC species from which the amplification products are generated may be identified or distinguished by hybridization to assay probes in the detection portion of the assay. For detection by hybridization, a detector probe (e.g., SEQ ID NO:13) is typically tagged with a detectable label. The detectable label is a moiety which can be detected either directly or indirectly as an indication of hybridization of the probe to the target nucleic acid. For direct detection of the label, probes may be tagged with a radioisotope and detected by autoradiography or tagged with a fluorescent moiety and detected by fluorescence as is known in the art. Alternatively, the probes may be indirectly detected by tagging with a label which requires additional reagents to render it detectable. Indirectly detectable labels include, for example, chemiluminescent agents, enzymes which produce visible reaction products and ligands (e.g., biotin, avidin, streptavidin, haptens, antibodies or antigens) which may be detected by binding to labeled specific binding partners (e.g., antibodies or antigens/haptens). Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonudeotides are well known in the art and any of these methods are suitable for use in the present invention.

One method for detecting amplification products employs polymerase extension of a primer specifically hybridized to the assay region. The palmer is labeled as described above, e.g., with a radioisotope, so that the label is incorporated with the primer into an amplicon-specific extension product. Detection by primer extension is described by G. Walker, et al. (1992. *Nuc. Acids Res.* and *PNAS*, supra). SEQ ID NO:13 may be used as a primer extension detector probe in conjunction with the amplification primers of the invention for detection of amplified BCG 85-B targets indicating the presence of the target from at least one MAC species. A second method for detecting amplification products is a chemiluminescent assay in which amplified products are detected using a biotinylated oligonucleotide capture probe and an enzyme-conjugated oligonucleotide detector probe as described by C. A. Spargo, et al. (1993. *Molec. Cell. Probes* 7, 395–404). After hybridization of these two probes to different sites in the assay region, the complex is captured on a streptavidin-coated microwell plate, and the chemiluminescent signal is developed and read in a luminometer. SEQ ID NO :13 may also be used as a detector probe (linked to a detectable label) or a capture probe (linked to a ligand suitable for solid phase capture) in this type of capture/detector assay.

By routine analysis of the of the assay region of the BCG 85-B target sequence of the invention, additional assay probes may be designed for detection of *M. avium*, *M. paratuberculosis* and/or *M. intracellulare* amplification products using the sequence information provided herein. SEQ ID NO:13 detects the target of all three MAC species when used as a detector probe. However, because the assay regions of the amplification products in *M. avium* and *M. intracellulare* differ from each other at several nucleotide positions, the species may also be distinguished using an assay probe specific for the assay region of the desired target.

EXAMPLE 1

The sensitivity of detection of the BCG 85-B target in MAC species was tested to determine the minimum initial genome copy number of *M. avium* ATCC 25291 and *M. intracellulare* ATCC 13950 which could be detected by SDA. Mycobacterial genomic DNA was isolated and diluted in 50 ng of human placental DNA. SDA reactions were performed essentially as described by G. Walker, et al. (1992. *Nucl. Acids Res.*, supra) or as disclosed in published European Patent Application 0 684 3 15 using $10^6$, $10^5$, $10^4$, $10^3$, $10^2$ and 0 initial mycobacterial genomes per reaction and the restriction endonuclease appropriate for the particular primer pair being tested. The tSDA reactions included an additional dilution containing 10 initial genomes. To facilitate decontamination of subsequent amplification reactions, dUTP was substituted for TTP as described in published European patent application 0 624 643. Prior to addition of enzymes and initiation of the amplification reaction, the samples were boiled for 2 min., then incubated at 41° C. for 2 min. with 1 unit UNG to degrade any contaminating amplicons. After a 30 min. incubation with UNG the samples were equilibrated for 5 min. at the appropriate temperature for the amplification reaction and the enzymes were added. For conventional SDA reactions, the reaction mixture was equilibrated at 41° C. HincII and $exo^-$ Klenow polymerase were then added and the amplification reaction was allowed to proceed for 2 hours at 41° C. tSDA reactions contained BsoBI and Bst polymerase and were incubated at 52° C. for 30 min. Amplification was terminated by boiling the sample for 5 min. The amplified product was detected by hybridization of SEQ ID NO:13 labeled at the 5' end with $^{32}P$. The hybridized detector probe was extended to diagnostic length using T4 polymerase (37° C., 10 min.). Extension was terminated by addition of 5 μL of 50% urea, 0.5 X TBE, 10 mM $Na_2EDTA$, 0.05% bromophenol blue/cylene cyanol. Extension products were analyzed by polyacrylamide gel electrophoresis and autoradiography.

On autoradiography, amplification primer pair SEQ ID NO:1/SEQ ID NO:2 the minimum initial target level detected was 100 for *M. avium* and 1000 for *M. intracellulare*, indicating a sensitivity of 1–100 and 100–1000, respectively. The minimum number of initial targets detected in tSDA was as follows:

| PRIMER PAIR | # INITIAL GENOMES | |
|---|---|---|
| | *M. avium* | *M. intracellulare* |
| SEQ ID NO: 3/SEQ ID NO: 7 | $10^2$ | $10^2$ |
| SEQ ID NO: 3/SEQ ID NO: 8 | $10^2$ | $10^2$ |
| SEQ ID NO: 4/SEQ ID NO: 7 | $10^3$ | $10^2$ |
| SEQ ID NO: 4/SEQ ID NO: 8 | $10^2$ | $10^2$ |

The sensitivity was therefore estimated to be between 10 and 100 initial targets for all primer pairs in *M. intracellulare*, and for SEQ ID NO:3/SEQ ID NO:7, SEQ ID NO:3/SEQ ID NO:8 and SEQ ID NO:4/SEQ ID NO:8 in *M. avium*. SEQ ID NO:4/SEQ ID NO:7 gave an assay sensitivity of 100–1000 initial targets in *M. avium*.

EXAMPLE 2

The MAC-specificity of the assay for BCG 85-B target amplification was tested in the 28 MAC serovars described by Inderlied, et at., supra. Cell lysates of each serovar containing $10^5$ genome copies were amplified in conventional SDA and tSDA reactions using the SEQ ID NO:1/SEQ D NO:2 and SEQ D NO:4/SEQ D NO:8 amplification primer pairs. Amplification-and detection of amplification products were as previously described.

The BCG 85-B target was detectably amplified in each of the 28 MAC serovars by tSDA and conventional SDA. The species and genus cross-reactivity of the amplification primers was then tested using the SEQ ID NO:1/SEQ ID NO:2 primer pair in the following organisms, amplifying $10^7$ genome copies per reaction by conventional SDA. The mycobacteria tested were *M. chelonae* (TMC 1453), *M. fortuitum* (TMC 2808), *M. gastri* (LCDC 1301), *M. gordonae* (TMC 1318), *M. kansasii* (TMC 1201), *M. marinum* (LCDC 801), *M. microti* (LCDC 203), *M. scrofulaceum* (TMC 1302), *M. tuberculosis* (VA 44), *M. xenopi* (LCDC 1901), *M. bovis* (CDC 52), *M. bovis*-BCG (CDC 4), *M. africanum (ATCC* 35711), *M. malmoense* (BDDIS 3472), *M. flavescens* (LCDC 2601), *M. terrae* (BDDIS 3010), *M. hemophilum* (ATCC 27548), *M. genevense* (PIP.) and *M. szulgai* (TMC 1328). The non-mycobacterial species tested were *Corynebacterium diphtheriae* (ATCC 11913), *Corynebacterium xerosis* (ATCC 373), *Corynebacterium pseudodiphtheriticum* (ATCC 10700), *Nocardia asteroides* (ATCC 3308), *Nocardia brasiliensis* (ATCC 19296), *Norcardia orientalis* (ATCC 19795), *Streptomyces somaliensis* (ATCC 13201), *Streptomyces griseus* (ATCC 10137), *Streptomyces albus* (ATCC 3004), *Streptomyces gedanensis* (ATCC 4880), *Actinomyces israelii* (ATCC 10049), *Eubacterium lentum* (ATCC 43055), *Rhodococcus equi* (ATCC 6939), *Rhodococcus rhodochrous* (ATCC 13808), *Propionibacterium acnes* (ATCC 6919), *Actinoplanes auranticolor* (ATCC 15330), *Streptosporangium viridialbum* (ATCC 33328) and *Streptoverticillium alboverticillatum* (ATCC 29818). The foregoing organisms, as well as *M. smegmatis* (TMC 1533) and *M. simiae (DIS* 2300, DIS 2301 and DIS 2308), were also tested in tSDA using SEQ ID NO:4/SEQ ID NO:8. *M. avium* (ATCC 25291), *M. intracellulare* (ATCC 13950) and *M. paratuberculosis* (Linda) were included as positive controls.

No amplification products were detected in any of the non-mycobacterial species tested in either conventional or thermophilic SDA. Of the mycobacteria, detectable amplification occurred only in the three MAC species and *M. szulgai* using conventional SDA. In tSDA, *M. szulgai* and *M. simiae* (DIS 2308) were positive in addition to MAC. Further investigation revealed that both the *M. szulgai* and *M. simiae* (DIS 2308) cultures and/or DNA samples had been contaminated with *M. intracellulare*, and the initial result was therefore attributed to a false positive. *M. terrae, M. flavescens* and *M. malmoense* were weakly positive in tSDA, but could be easily distinguished from the strong positive result obtained for the MAC species. This minimal level of detection in three non-MAC species under the conditions of tSDA is therefore considered to be insubstantial and does not prevent use of the primers and probes of the invention for complex-specific detection of MAC targets.

What is claimed is:

1. An oligonucleotide consisting of a target binding sequence selected from the group consisting of the target binding sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10, and, optionally, a sequence required for an amplification reaction.

2. The oligonucleotide of claim 1 wherein the sequence required for the amplification reaction is a restriction endonuclease recognition site which is capable of being nicked by a restriction endonuclease during Strand Displacement Amplification.

3. The oligonucleotide of claim 2 selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

4. An oligonucleotide selected from the group consisting of SEQ ID NO:11, SEQ ID NO:12, SEQ ID NO:13, SEQ ID NO:14, SEQ ID NO:15, SEQ ID NO:17 and SEQ ID NO:18.

5. A method for amplifying a target nucleic acid of the *Mycobacterium avium* complex comprising:
 a) hybridizing to the target nucleic acid
  i) a first amplification primer consisting of a target binding sequence selected from the group consisting of the target binding sequences of SEQ ID NO:1, SEQ ID NO:3, SEQ ID NO:4, SEQ ID NO:5 and SEQ ID NO:6 and, optionally, a sequence required for an amplification reaction, and
  ii) a second amplification primer consisting of a target binding sequence selected from the group consisting of the target binding sequences of SEQ ID NO:2, SEQ ID NO:7, SEQ ID NO:8, SEQ ID NO:9 and SEQ ID NO:10 and, optionally the sequence required for the amplification reaction, and;
 b) extending the hybridized first and second amplification primers on the target nucleic acid whereby the target nucleic acid is amplified.

6. The method of claim 5 further comprising detecting the amplified target nucleic acid by hyridization to an assay probe.

7. The method of claim 6 wherein the assay probe consists of SEQ ID NO:13 tagged with a detectable label.

8. The method of claim 6 wherein the amplified target nucleic acid is captured for detection by hybridization to a capture probe.

9. The method of claim 8 wherein the capture probe consists of SEQ ID NO:13 tagged with a ligand.

10. The method of claim 5 wherein the sequence required for the amplification reaction is a recognition site for a restriction endonuclease which is capable of being nicked by the restriction endonuclease during Strand Displacement Amplification.

11. The method of claim 10 wherein the first amplification primer consists of SEQ ID NO:1, SEQ ID NO:3, SEQ ID NO:4, SEQ ID NO:5 or SEQ ID NO:6 and the second amplification primer consists of SEQ ID NO:2, SEQ ID NO:7, SEQ ID NO:8, SEQ ID NO:9 or SEQ ID NO:10.

12. The method of claim 11 wherein the hybridized first and second amplification primers are displaced from the target nucleic acid by extension of a first bumper primer consisting of SEQ ID NO:11 and a second bumper primer consisting of SEQ ID NO:12.

13. The method of claim 5 wherein the target nucleic acid is amplified by the Polymerase Chain Reaction.

14. A method for amplifying a target nucleic acid of the *Mycobacterium avium* complex comprising:
 a) hybridizing to the target nucleic acid
  i) a first amplification primer consisting of SEQ ID NO:1, SEQ ID NO:3, SEQ ID NO:4, SEQ ID NO:5 or SEQ ID NO:6, and
  ii) a second amplification primer consisting of SEQ ID NO:2, SEQ ID NO:7, SEQ ID NO:8, SEQ ID NO:9 or SEQ ID NO:10, and;
 b) amplifying the target nucleic acid in a Strand Displacement Amplification reaction.

15. The method of claim 14 further comprising detecting the amplified target nucleic acid by hybridization to a detector probe.

16. The method of claim 15 wherein the detector probe consists of SEQ ID NO:13 tagged with a detectable label.

17. The method of claim 15 wherein the amplified target nucleic acid is captured for detection by hybridization to a capture probe.

18. The method of claim 17 wherein the capture probe consists of SEQ ID NO:13 tagged with a ligand.

19. The method of claim 14 wherein the first amplification primer consists of SEQ ID NO:1 and the second amplification primer consists of SEQ ID NO:2, or the first amplification primer consists of SEQ ID NO:4 and the second amplification primer consists of SEQ ID NO:8.

20. The method of claim 19 wherein the hybridized first and second amplification primers are displaced from the target nucleic acid by extension of a first bumper primer consisting of SEQ ID NO:11 and a second bumper primer consisting of SEQ ID NO:12.

21. A method for simultaneously amplifying a first and a second target comprising:
 a) hybridizing a first amplification primer to the first target, the first amplification primer comprising the target binding sequence of SEQ ID NO:1 or SEQ ID NO:2 and a recognition site for a restriction endonuclease which is capable of nicking one strand of a double-stranded hemimodified recognition site for the restriction endonuclease, extending the first amplification primer to produce a first extension product and displacing the first extension product;
 b) hybridizing to the first extension product a first adapter primer consisting of the target binding sequence of SEQ ID NO:2 or the target binding sequence of SEQ ID NO:1 and a first adapter sequence substantially identical to a target binding sequence of a second amplification primer which hybridizes to the second target, the second amplification primer further comprising the recognition site for the restriction endonuclease, extending the first adapter primer to produce a second extension product and displacing the second extension product;
 c) hybridizing the second amplification primer to the second target, extending the second amplification primer to produce a third extension product and displacing the third extension product;

d) hybridizing to the third extension product a second adapter primer consisting of a target binding sequence which hybridizes to the third extension product and a second adapter sequence substantially identical to the target binding sequence of SEQ ID NO:1 or the target binding sequence of SEQ ID NO:2, extending the second adapter primer to produce a fourth extension product, displacing the fourth extension product, and;

e) simultaneously amplifying the second and fourth extension products using the first and second amplification primers.

22. The method of claim 21 further comprising detecting the amplified first or second target.

23. A method for simultaneously amplifying a first and a second target comprising:

a) hybridizing a first amplification primer to the first target, the first amplification primer comprising the target binding sequence of SEQ ID NO:4 or SEQ ID NO:8 and a recognition site for a restriction endonuclease which is capable of nicking one strand of a double-stranded hemimodified recognition site for the restriction endonuclease, extending the first amplification primer to produce a first extension product and displacing the first extension product;

b) hybridizing to the first extension product a first adapter primer consisting of the target binding sequence of SEQ ID NO:8 or the target binding sequence of SEQ ID NO:4 and a first adapter sequence substantially identical to a target binding sequence of a second amplification primer which hybridizes to the second target, the second amplification primer further comprising the recognition site for the restriction endonuclease, extending the first adapter primer to produce a second extension product and displacing the second extension product;

c) hybridizing the second amplification primer to the second target, extending the second amplification primer to produce a third extension product and displacing the third extension product;

d) hybridizing to the third extension product a second adapter primer consisting of a target binding sequence which hybridizes to the third extension product and a second adapter sequence substantially identical to the target binding sequence of SEQ ID NO:4 or the target binding sequence of SEQ ID NO:8, extending the second adapter primer to produce a fourth extension product, displacing the fourth extension product, and;

e) simultaneously amplifying the second and fourth extension products using the first and second amplification primers.

24. The method of claim 23 wherein the first amplification primer consists of SEQ ID NO:8, the first adapter primer consists of SEQ ID NO:18, the second amplification primer consists of SEQ ID NO:16, and the second adapter primer consists of SEQ ID NO:17.

25. The method of claim 23 further comprising detecting the amplified first or second target.

* * * * *